US005630786A

United States Patent [19]
Griffin et al.

[11] Patent Number: 5,630,786
[45] Date of Patent: May 20, 1997

[54] BORON NEUTRON CAPTURE ENHANCEMENT OF FAST NEUTRON THERAPY

[75] Inventors: Brian R. Griffin, Edmonds; George E. Laramore, Seattle, both of Wash.

[73] Assignee: IONIX Corporation, Seattle, Wash.

[21] Appl. No.: 267,350

[22] Filed: Jun. 27, 1994

[51] Int. Cl.$^6$ ..................................................... A61N 5/00
[52] U.S. Cl. .............................. 600/3; 128/659; 128/898; 424/1.11
[58] Field of Search ........................ 600/1–3; 424/1.11; 128/659, 898, 654; 604/20, 49

[56] References Cited

U.S. PATENT DOCUMENTS

| | | | |
|---|---|---|---|
| 4,466,952 | 8/1984 | Hadd | 424/1.1 |
| 4,516,535 | 5/1985 | Russell | 128/1.1 |
| 4,675,150 | 6/1987 | Russell | 376/340 |
| 4,959,356 | 9/1990 | Miura | 514/64 |
| 5,144,026 | 9/1992 | Gabel | 540/500 |
| 5,149,801 | 9/1992 | Kahl | 540/145 |
| 5,328,678 | 7/1994 | Fujii | 424/1.21 |

FOREIGN PATENT DOCUMENTS

0272091  6/1988  European Pat. Off. .

OTHER PUBLICATIONS

Hatanaka, H., *Boron–Nautron Capture Therapy for Tumors* (H. Hatanaka, Ed.), Nishimura Co. Ltd., Nigata, Japan, p. 5 (1986).

Kruger, P.G., "Some Biological Effects of Nuclear Disintegration Products on Neoplastic Tissue," *Proc. Natl. Acad. Sci.*, 26:181–192 (1940).

Zahl, P.A. et al., "Some in vivo Effects of Localized Nuclear Disintegration Products on a Transplantable Mouse Sarcoma," *Proc. Natl. Acad. Sci.*, 26:589–598 (1940).

Farr, L.E. et al., "Neutron Capture Therapy With Boron in the Treatment of Glioblastoma Multiforme," *Am. J. Roentgenol.*, 71:279–291 (1954).

Godwin, J.T. et al., "Pathological Study of Eight Patients With Glioblastoma Multiforme Treated By Neutron Capture Therapy Using Boron 10," *Cancer (Phila.)*, 8:601–615 (1955).

Asbury, A.K. et al., "Neuropathologic Study of Fourteen Cases of Malignant Brain Tumor Treated by Boron–10 Slow Neutron Capture Radiation," *J. Neuropathol. Exp. Neurol.*, 31:278–303 (1972).

Brownell, G.L. et al., "Cancer of the Central Nervous System: A Reassessment of Neutron Capture Therapy in the Treatment of Cerebral Gliomas," *Seventh National Cancer Conference Proceedings*, Philadelphia: Lippincott, 827–837 (1973).

(List continued on next page.)

*Primary Examiner*—Corrine M. McDermott
*Assistant Examiner*—Chalin Smith
*Attorney, Agent, or Firm*—Christensen O'Connor Johnson & Kindness PLLC

[57]  ABSTRACT

Fast neutron therapy is significantly enhanced by irradiating target cells, either in vitro or in vivo, with fast neutrons in the presence of a boron neutron capture agent having a plurality, and preferably at least nine, of $^{10}$B atoms per molecule of the agent. In other aspects, tumor cells are treated in vivo by administering to a human or non-human animal a boron neutron capture agent having at least nine $^{10}$B atoms per molecule of the agent in an amount effective to associate the boron neutron capture agent with the tumor cells, and then irradiating the tumor cells with fast neutrons. Suitable boron neutron capture agents may be based on polyhedral borane anion derivatives, on derivatives that comprise two polyhedral borane anion cages linked together to form a structure comprising 20 boron atoms, on polyhedral carboranes such as compounds of the formulas closo—$C_2B_{n-2}H_n$, closo—$CB_{n-1}H_n^-$, or nido—$C_2B_{n-3}H_n^-$, on oligomeric peptides constructed from boron-rich α-amino acids, or on boron enriched oligophosphates.

21 Claims, 1 Drawing Sheet

OTHER PUBLICATIONS

Hatanaka, H., "A Revised Boron Neutron Capture Therapy For Malignant Brain Tumors. II.," *J. Neurol.*, 209:81–94 (1975).

Hatanaka, H. and Sano, K., "A Revised Boron Neutron Capture Therapy for Malignant Brain Tumors. I.," *J. Neurol.*, 204:309–332 (1973).

Mishima, Y. et al., "First Human Clinical Trial of Melanoma Capture. Diagnosis and Therapy," *Strahlenther. Onkol.*, 165:251–254 (1989).

Stone, R.S., "Neutron Therapy and Specific Ionization," *Am. J. Roentgenol.*, 59:771–785 (1948).

Laramore, G.E., "Injury to the Central Nervous System After High LET Radiation," in *Radiation Injury to the Nervous System* (P.H. Gutin et al., Eds.), Raven Press Ltd., New York, NY, pp. 341–360 (1991).

Laramore, G.E. and Austin–Seymour, M.M., "Fast Neutron Radiotherapy in Relation to the Radiation Sensitivity of Human Organ Systems," *Advances in Radiation Biology* 15:153–193 (1992).

Griffin, T.W. et al., "Neutron vs Photon Irradiation of Inoperable Salivary Gland Tumors: Results of an RTOG–MRC Cooperative Randomized Study," *Int. J. Radiat. Oncol. Biol. Phys.*, 15:1085–1090 (1988).

Laramore, G.E. et al., "Fast Neutron Radiotherapy for Locally Advanced Prostate Cancer," *Am. J. Clin. Oncol. (CCT)*, 16:164–167 (1993).

Russell, K.J. et al., "Eight Years Experience With Neutron Radiotherapy in the Treatment of Stages C and D Prostate Cancer: Updated Results of the RTOG 7704 Randomized Clinical Trial," *The Prostate*, 11:183–193 (1987).

Laramore, G.E. et al., "Fast Neutron Radiotherapy For Sarcomas of Soft Tissue, Bone, and Cartilage," *Am. J. Clin. Oncol. (CCT)*, 12:320–326 (1989).

Waterman, F.M. et al., "The Use of $^{10}$B to Enhance the Tumour Dose in Fast–Neutron Therapy," *Phys. Med. Biol.*, 23(4):592–602 (1978).

Sauerwein, W. et al., "Neutron Capture Therapy Using a Fast Neutron Beam: Clinical Considerations and Physical Aspects," *Strahlenther. Onkol.*, 165:208–210 (1989).

Ziegler, W. et al., "Fast Neutrons From the Essen Cyclotron Can Be Used Successfully For Neutron Capture Experiments In Vitro," *Strahlenther. Onkol.*, 165:210–212 (1989).

Wootton, P. et al., "Boron Neutron Capture Enhancement of the Tumor Dose in Fast Neutron Therapy Beams," *Proceedings of the Fourth Internat. Symposium on Neutron Capture Therapy For Cancer*, Sydney, Australia, Dec. 4–7, 1990.

Sauerwein, W. et al., "Boron Neutron Capture Therapy (BNCT) Using Fast Neutrons: Effects in Two Human Tumor Cell Lines," *Strahlenther. Onkol.*, 166:26–29 (1990).

Laramore, G.E. et al., "Boron Neutron Capture Therapy: A Means of Increasing the Effectiveness of Fast Neutron Radiotherapy," in *Radiation Research: A Twentieth–Century Perspective*, Proceedings of the 9th ICRR (W.C. Dewey et al., Eds.), Academic Press, San Diego, CA, pp. 617–622 (1991).

Wootton, P. et al., "Boron Neutron Capture Enhancement of the Tumor Dose in Fast Neutron Therapy Beams," *Progress in Neutron Capture Therapy for Cancer* (B.J. Allen et al., Eds.), Plenum Press, New York, NY, pp. 195–198 (1992).

Laramore, G.E. et al., "Boron Neutron Capture Therapy: A Mechanism for Achieving a Concomitant Tumor Boost in Fast Neutron Radiotherapy," *Int. J. Radiat. Oncology Biol. Phys.*, 28:1135–1142 (1994).

Pitochelli, A.R. and Hawthorne, M.F., "The Isolation of the Icosahedral $B_{12}H_{12}^{-2}$ Ion," *J. Am. Chem. Soc.*, 82:3228 (1960).

Miller, H., "Synthesis of Polyhedral Boranes," *J. Am. Chem. Soc.*, 85:3885–3886 (1963).

Hawthorne, M.F. and Pitochelli, A.R., "The Reactions of Bis–Acetonitrile Decaborane with Amines," *J. Am. Chem. Soc.*, 81:5519 (1959).

Lipscomb, W.N. et al., "Probable Structure of the $B_{10}H_{10}^{-2}$ Ion," *J. Am. Chem. Soc.*, 81:5833 (1959).

Knoth, W.H. et al., "Chemistry of Boranes XIX. Derivative Chemistry of $B_{10}H_{10}^{-2}$ and $B_{12}H_{12}^{-2}$," *J. Am. Chem. Soc.*, 86:3973–3983 (1964).

Tolpin, E.I. et al., "Synthesis and Chemistry of Mercaptoundeca–hydro–*closo*–dodecaborate(2–)," *Inorg. Chem.*, 17(10):2867–2873 (1978).

Hawthorne, M.F., "The Role of Chemistry in the Development of Boron Neutron Capture Therapy of Cancer," *Angewandte Chemie, International Edition in English*, 32:950–984 (1993).

Dunks, G.B. and Hawthorne, M.F., "The Non–Icosahedral Carboranes: Synthesis and Reactions," *Accts. Chem. Res.*, 6:124–131 (1973).

Grafstein, D. and Dvorak, J., "Neocarboranes, a New Family of Stable Organoboranes Isomeric with the Carboranes," *Inorg. Chem.*, 2(6):1128–1133 (1963).

Knoth, W.H., "1–$B_9H_9$CH– and $B_{11}H_{11}$CH–," *J. Am. Chem. Soc.*, 89:1274–1275 (1967).

Morris, J. et al., "Preparation of New Boron Compounds With Potential for Application in $^{10}$B NCT: Derivatives of Monocarbon Carboranes," in *Progress in Neutron Capture Therapy of Cancer* (B.J. Allen et al., Eds.), Proceedings of the Fourth International Symposium on Neutron Capture Therapy of Cancer, Plenum Press, New York, NY, pp. 215–217 (1992).

Varadarajan, A. and Hawthorne, M.F., "Novel Carboranyl Amino Acids and Peptides: Reagents for Antibody Modification and Subsequent Neutron–Capture Studies," *Bioconjugate Chem.*, 2(4):242–253 (1991).

Paxton, R.J. et al., "Carboranyl Peptide–Antibody Conjugates for Neutron–Capture Therapy: Preparation, Characterization, and In Vivo Evaluation." *Bioconjugate Chem.*, 3(3):241–247 (1992).

Kane, R. et al., "Automated Syntheses of Carborane–Derived Homogeneous Oligophosphates: Reagents for Use in the Immuno–protein–Mediated Boron Neutron Capture Therapy of Cancer," *J. Am. Chem. Soc.*, 115(9):8853–8854 (1993).

Kane, R. et al., "Solution–Phase Synthesis of Boron–Rich Phosphates," *J. Org. Chem.*, 58(12):3227–3228 (1993).

Kane, R. et al., "Novel Carboranyl Diols and Their Derived Phosphate Esters," *Advances in Neutron Capture Therapy* (A.H. Soloway et al., Eds.), Plenum Press, New York, NY, pp. 293–296 (1993).

Shelly, K. et al., "Model Studies Directed Toward the Boron Neutron–Capture Therapy of Cancer: Boron Delivery to Murine Tumors With Liposomes," *Proc. Natl. Acad. Sci. USA*, 89:9039–9043 (1992).

Elstad, C.A. et al., "In vivo and in vitro Uptake of Boronated Compounds by B16–BL6 Murine Melanoma," *Advances in Neutron Capture Therapy* (A.H. Soloway et al., Eds.), Plenum Press, New York, NY, pp. 619–622 (1993).

DeBenedetti, S., "Nuclear Reactions and Nuclear Models," In *Nuclear Interactions*, John Wiley & Sons, New York, NY, pp. 338–344 (1964).

Soloway, A.H. et al., "Evaluation of Boron Compounds for Use in Neutron Capture Therapy of Brain Tumors. I. Animal Investigations," *J. Pharma. Exp. Thera.*, 134:117–122 (1961).

Sweet, W.H. et al., "Boron–Slow Neutron Capture Therapy of Gliomas," *Acta Radiol.*, 1:114–121 (1963).

BORON NEUTRON CAPTURE ENHANCEMENT OF FAST NEUTRON THERAPY

FIELD OF THE INVENTION

The present invention relates to the use of boron-containing agents in boron neutron capture therapy killing of target cells. More particularly, this invention relates to boron neutron capture enhancement of fast neutron radiation therapy.

BACKGROUND OF THE INVENTION

Shortly after the neutron was discovered by Chadwick in 1932, its potential use in the treatment of human malignancies was realized. The concept of nuclei having a characteristic effective cross-sectional area, expressed as units of $10^{-24} cm^2$ known as barn units, was introduced with this early work. The effective nuclear cross section of boron for neutron capture was known to be exceptionally large while borons neighbors in the periodic table, nitrogen and carbon, exhibited nuclear cross sections which were comparatively quite small.

Taylor, *Proc. Roy. Soc.*, A47: 873 (1935) described the capture of thermal neutrons by $^{10}B$ nuclei followed by the production of $^4He^{2+}$ (α-particles) and $^7Li^{3+}$ with about 2 MeV of kinetic energy distributed between these two heavy ion products. It was also determined (Taylor, supra) that the translational range of the product ions was particularly short; about 7.6 μ in photographic gelatin and 1.1 cm in air. Consequently, the lithium ion and the α-particle products were short-range, energetic species capable of imparting immense local damage to organic materials through ionization processes.

The boron neutron capture (BNC) reaction obtained with thermal, 293 K (0.025 eV), neutrons may be represented as shown in Equation (1):

$$^{10}B + ^1n_{th} \longrightarrow \quad (1)$$

The $^{11}B$ nucleus is incapable of undergoing a BNC reaction while the effective nuclear cross section of $^{10}B$ is 3837 barns.

Two other nuclides, $^1H$ and $^{14}N$, are abundant in tissue and participate in important neutron capture side-reactions which occur during BNCT and thus contribute important doses of background radiation to the subject. These two neutron capture reactions play a role, not because of enhanced nuclear cross sections of the target nuclei, but due to their very high concentrations in tissue. As disclosed in H. Hatanaka, *Boron-Neutron Capture Therapy for Tumors* (H. Hatanaka, Ed.), Nishimura Co. Ltd., Nigata, Japan, p. 5 (1986), the neutron capture reactons of $^1H$ and $^{14}N$ are as shown in Equations (2a) and (2b), respectively:

where * represents a transient, excited state. The passage of a neutron through hydrogen-rich media, such as tissue, results in the slowing and scattering of these neutrons by collisions with nuclear protons of the H-atoms. Occasionally, a slowly moving neutron will be captured by such a proton and produce a deuteron accompanied by characteristic gamma radiation which contributes to the total radiation dose. In another competing capture reaction, the nitrogen atoms available in tissue may capture a low-energy neutron and generate $^{14}C$ and an 0.63 MeV (kinetic energy) proton. The kinetic energy imparted to the $^7Li^{3+}$ and $^4He^{2+}$ ions derived from the BNC reaction and that similarly associated with the proton and γ-photons, produced as shown in (2a) and (2b), is transferred to the surrounding media. Since all of these energetic nuclear reaction products, with the exception of the γ-photons, are heavy particles, this kinetic energy transfer is rapid and takes place along a very short path length. The rate of linear energy transfer, LET, of these particles is characteristically high and the immense energy of these reactions is therefore deposited in a very small volume. As an example, the $^7Li^{3+}$ and $^4He^{2+}$ ions generated in the BNC reaction generate ionization tracks about 0.01 mm long or the equivalent of approximately one cell diameter. Thus, the high LET characteristic of particles produced by nuclear reactions which occur within tissue are especially lethal to affected cells due to the high density of deposited energy.

Ideally, those cells which carry large numbers of $^{10}B$ nuclei are subject to destruction by BNC while neighboring cells that are free of $^{10}B$ are spared, save for the contribution of the background $^1H(n,\gamma)^2H$ and $^{14}N(n,p)^{14}C$ reactions. In order for the delivery of $^{10}B$ to tumor cells to achieve this desired effect in BNCT the selectivity of boron delivery to tumor versus normal tissue, which is subject to neutron irradiation, should be as great as possible. In addition, the actual concentration of $^{10}B$ in tumor must be sufficiently high to offer a localized binary therapeutic effect well above the background radiation dose delivered by the $^1H(n,\gamma)^2H$ and $^{14}N(n,p)^{14}C$ neutron capture processes shown above. The minimum generally accepted $^{10}B$ concentration necessary for effective BNC has been commonly believed to be between 10 and 30 μg $^{10}B$/g tumor depending upon the precise location of the $^{10}B$ with respect to vital components of the tumor cell structure. As the position of the $^{10}B$ nuclei is changed from the external cell wall to the cytoplasm to the nucleus of the cell, the required concentration of $^{10}B$ for effective BNCT decreases, as expected. Thus, cell wall-bound $^{10}B$ might require 30 ppm or greater concentrations while $^{10}B$ localized within the nucleus of the tumor cell might only require a concentration of 10 ppm or less. An additional factor is the steady state concentration of thermal neutrons in the targeted volume of tissue since very low neutron intensities require proportionally longer irradiation times to produce the required number of BNC events for effective therapy.

In 1936 Locher (G. L. Locher, "Biological Effects and Therapeutic Possibilities of Neutrons," *Am. J. Roentgenol.* 36: 1–13 (1936)) proposed using the boron neutron capture reaction in the treatment of tumors. This approach was termed boron neutron capture therapy (BNCT) and a few years later Kruger and Zahl et al. (P. G. Kruger, "Some Biological Effects of Nuclear Disintegration Products on Neoplastic Tissue," *Proc. Natl. Acad. Sci.* 26: 181–192 (1940); P. A. Zahl et at., "Some in vivo Effects of Localized Nuclear Disintegration Products on a Transplantable Mouse Sarcoma," *Proc. Natl. Acad. Sci.* 26: 589–598 (1940)) experimentally verified this concept and demonstrated the biological effectiveness of the fission fragments produced by slow neutrons interacting with $^{10}B$. The first clinical trials for human malignancies were carded out in the 1950s using a reactor beam at the Brookhaven National Laboratories to treat malignant gliomas of the brain. In these initial trials boric acid derivatives were used as the $^{10}$B carrier agent (L. E. Farr et at., "Neutron Capture Therapy With Boron in the Treatment of Glioblastoma Multiforme," *Am. J. Roentgenol.* 71: 279–291 (1954); J. T. Godwin et al., "Pathological Study of Eight Patients With Glioblastoma Multiforme Treated By Neutron Capture Therapy Using Boron 10," *Cancer (Phila.)* 8: 601–615 (1955)). Because of the attenuation of the thermal neutrons in tissue and problems with necrosis of the calvarium, subsequent trials in the 1960s at the Massachusetts Institute of Technology Research Reactor used craniotomies both to remove as much tumor as possible and to expose the tumor bed directly to the slow neutron beam. Unfortunately, these trials showed no therapeutic benefit from this form of treatment and moreover, showed considerable damage to the endothelial linings of the blood vessels (A. K. Asbury et al., "Neutopathologic Study of Fourteen Cases of Malignant Brain Tumors Treated by Boron-10 Slow Neutron Capture Therapy," *J. Neuropathol. Exp. Neurol.* 31: 278–303 (1972); G. L. Brownell et al., "A Reassessment of Neutron Capture Therapy in the Treatment of Cerebral Gliomas," *Seventh National Cancer Conference Proceedings*, Philadelphia: Lippincott, 827–837 (1973)). This was attributed both to the high concentration of $^{10}$B in the blood at the time of treatment and to the relatively poorly penetrating characteristics of the collimated reactor beams used for treatment. Subsequently, H. Hatanaka, "A Revised Boron Neutron Capture Therapy For Malignant Brain Tumors. II.," *J. Neurol.* 209: 81–94 (1975), and H. Hatanaka and K. Sano, "A Revised Boron Neutron Capture Therapy for Malignant Brain Tumors. II.," *J. Neurol.* 204: 309–332 (1973), reported Japanese clinical trials of BNCT using $Na_2B_{12}H_{11}SH$ (i.e., BSH) as a carrier agent. Trials have continued to the present time and the data indicates several longterm "cures" of patients with documented glioblastoma multiforme (H. Hatanaka, *Boron-Neutron Capture Therapy for Tumors* (H. Hatanaka, Ed.), Nishimura Co. Ltd., Nigata, Japan, p. 5 (1986)). Trials have also been initiated in Japan for malignant melanoma using a boronated form of phenylalanine as the boron carrier (Y. Mishima et al., "First Human Clinical Trial of Melanoma Capture: Diagnosis and Therapy," *Strahlenther. Onkol.* 165: 251–254 (1989)).

Despite the conceptual appeal of this treatment, BNCT has yet to develop into a clinically useful therapy due to problems with boron delivery and difficulties in using thermal neutrons. A tumor-selective boron carder has yet to be fully developed. The clinical experiences using BNCT have noted significant skin and vascular tissue toxicity as a result of poor tumor specificity of the boron delivery agents. In addition, since the pathways of the $^{10}$B fission products are in the range of one cell diameter, traditional BNCT theoretically requires that every clonogenic tumor cell be labeled with $^{10}$B in order to achieve a tumor cure.

In parallel with this work, other investigators began to use high energy neutrons generated by a cyclotron as another form of external beam radiotherapy (R. S. Stone, "Neutron Therapy and Specific Ionization," *Am. J. Roentgenol.* 59: 771–785 (1940)). Like the situation with BNCT, the early clinical trials showed considerable toxicity and little efficacy and the field languished until the 1950s when mammalian cell culture techniques revealed critical differences between neutron and photon postirradiation cell survival curves. Clinical trials were resumed at Hammersmith Hospital in London, England in the 1960s and since that time over 15,000 patients have been treated with fast neutrons for various malignancies. This immense data base has enabled an accurate estimation of the tolerance of most clinically relevant normal tissues to fast neutron radiotherapy (G. E. Laramore, "Injury to the Central Nervous System After High LET Radiation," in *Radiation Injury to the Nervous System* (P. H. Gutin et at., Eds.), Raven Press, New York, N.Y., pp. 341–360 (1991); G. E. Laramore and M. Austin-Seymour, "Fast Neutron Radiotherapy in Relation to the Radiation Sensitivity of Human Organ Systems," in *Relative Radiosensitivies of Human Organ Systems, III. Advances in Radiation Biology* (K. I. Altman and J. Lett, Eds.), Academic Press, Orlando, Fla., 15: 153–193 (1992)). Based upon randomized clinical trials and single-institution experiences, fast neutrons appear to offer a therapeutic advantage compared to conventional, megavoltage photon irradiation for the following tumor systems: salivary gland tumors (T. W. Griffin et at., "Neutron vs. Photon Irradiation of Inoperable Salivary Gland Tumors: Results of an RTOG-MRC Cooperative Randomized Study," *Int. J. Radiat. Oncol. Biol. Phys.* 15: 1085–1090 (1988)), locally advanced prostate cancer (G. E. Laramore et al., "Fast Neutron Radiotherapy for Locally Advanced Prostate Cancer: Final Report of an RTOG Randomized Clinical Trial," *Am. J. Clin. Oncol. (CCT)* 16: 164–167 (1993); K. J. Russell et al., "Eight Years Experience With Neutron Radiotherapy in the Treatment of Stages C and D Prostate Cancer: Updated Results of the RTOG 7704 Randomized Clinical Trial," *Prostate* 11: 183–193 (1987)), and sarcomas of bone and soft tissue (G. E. Laramore et al., "Fast Neutron Radiotherapy For Sarcomas of Soft Tissue, Bone, and Cartilage," *Am. J. Clin. Conol. (CCT)* 12: 320–326 (1989)). In a randomized trial for patients with inoperable salivary gland tumors, initial tumor clearance rates at the primary site were 85% for neutron-treated patients compared to 33% for photon-treated patients (p=0.01), respective local-regional control rates at 2 years were 67% vs. 17% (p=0.005), and 2 year survivals were 62% vs. 25% (p=0.10). These results were consistent with historical data. Ten-year data continue to show a therapeutic advantage to fast neutrons for salivary gland tumors. In the case of locally advanced prostate cancer, a randomized, clinical trial compared a combination of neutrons and photons (i.e., mixed beam) with photons alone. At 10 years, local control rates were 63% for the mixed beam group compared to 52% for the photon group (p=0.05) and respective survival rates were 42% vs. 27% (p=0.05) (G. E. Laramore et al., "Fast Neutron Radiotherapy for Locally Advanced Prostate Cancer: Final Report of an RTOG Randomized Clinical Trial," in *J. Clin. Oncol. (CCT)* 16: 164–167 (1993)). In the case of sarcomas there have been no randomized clinical trials but a historical comparison between fast neutrons and conventional photon irradiation for inoperable tumor shows respective local control rates of 53% vs. 38% for soft tissue sarcomas, 55% vs. 21% for osteogenic sarcomas, and 49% vs. 33% for chondrosarcomas (G. E. Laramore et al., *Am. J. Clin. Oncol. (CCT)* 12: 320–326, supra)). For other tumor systems such as squamous cell tumors of the head and neck, esophageal carcinomas, and high grade gliomas of the brain, fast neutron radiotherapy has exhibited no improvement over conventional photon irradiation.

It has been previously proposed to utilize the boron neutron capture reaction to enhance fast-neutron therapy of malignant tumors. See, for example, F. M. Waterman et al., "The Use of $^{10}$B to Enhance the Tumor Dose in Fast-Neutron Therapy," *Phys. Med. Biol.* 23(4): 592–602 (1978); W. Saurwein et al., "Neutron Capture Therapy Using a Fast Neutron Beam: Clinical Considerations and Physical Aspects," *Strahlenther. Onkol.* 165: 208–210 (1989); W. Ziegler et al., "Fast Neutrons From the Essen Cyclotron Can Be Used Successfully For Neutron Capture Experiments In Vitro," *Strahlenther. Onkol.* 165: 210–212 (1989); P. Wootton et al., "Boron Neutron Capture Enhancement of the Tumor Dose in Fast Neutron Therapy Beams," *Proceedings of the Fourth Internat. Symposium on Neutron Capture Therapy For Cancer*, Sydney, Australia, Dec. 4–7, 1990; W. Sauerwein et al., "Boron Neutron Capture Therapy (BNCT) Using Fast Neutrons: Effects in Two Human Tumor Cell Lines," *Strahlenther. Onkol.* 166: 26–29 (1990); G. E. Laramore et al., "Boron Neutron Capture Therapy: A Means of Increasing the Effectiveness of Fast Neutron Radiotherapy," *Proceedings of the 9th ICRR*, W. C. Dewey et al., Eds., Academic Press, San Diego, Calif. (1991), pp. 617–622; P. Wootton et al., "Boron Neutron Capture Enhancement of the Tumor Dose in Fast Neutron Therapy Beams," *Progress in Neutron Capture Therapy for Cancer*, B. J. Allen et al., Eds., Plenum Press, New York (1992), pp. 195–198; and G. E. Laramore et al., "Boron Neutron Capture Therapy: A Mechanism for Achieving a Concomitant Tumor Boost in Fast Neutron Radiotherapy," *J. Radiation Oncology Biol. Phys.* 28: 1135–1142 (1994). Despite the advances that have been made in fast neutron therapy, most of the reported studies of enhancement of fast neutron therapy with $^{10}B$ BNCT have involved the treatment of cells in vitro, and the successful application of this technique in vivo remains highly problematical.

SUMMARY OF THE INVENTION

It has now been discovered that the effectiveness of fast neutron therapy can be significantly enhanced by irradiating target cells, either in vitro or in vivo, with fast neutrons in the presence of a boron neutron capture agent comprising a plurality, and preferably at least nine, of $^{10}B$ atoms per molecule of the agent. In other aspects, tumor cells in a human or non-human animal are treated by administering to the human or non-human animal a boron neutron capture agent comprising at least nine $^{10}B$ atoms per molecule of the agent in an amount effective to associate the boron neutron capture agent with the tumor cells, and then irradiating the tumor cells with fast neutrons. Suitable boron neutron capture agents may be based on polyhedral borane anion derivatives, such as closo-$B_{12}H_{12}^{2-}$; closo-$B_{10}H_{10}^{2-}$ or BSH ($B_{12}H_{12}SH^{2-}$), on derivatives that comprise two polyhedral borane anion cages linked together to form a structure comprising 20 boron atoms, on polyhedral carboranes such as compounds of the formulas closo-$C_2B_{n-2}H_n$ or closo-$CB_{n-1}H_n$, on oligomeric peptides constructed from boron-rich α-amino acids, or on compounds of the formula:

integer from 1 to 10 and n is an integer from 2 to 150, preferably from 20 to 100.

The isotopic content of the boron employed in the agents of the present invention is preferably enriched in $^{10}B$, and the boron containing agents can be administered either as free agents or in connection with other delivery vehicles, such as unilamellar or multilamellar vesicles, including liposomes.

BRIEF DESCRIPTION OF THE DRAWINGS

The foregoing aspects and other advantages of this invention will become more readily appreciated by reference to the following detailed description and accompanying drawings, wherein.

DETAILED DESCRIPTION OF THE PREFERRED EMBODIMENT

In accordance with the present invention, target cells are killed by irradiating the target cells, either in vitro or in vivo, with fast neutrons in the presence of a boron neutron capture agent comprising a plurality, and preferably at least nine, of $^{10}B$ atoms per molecule of the agent. In other aspects of the present invention, tumor cells in a human or non-human animal are treated by administering to the human or non-human animal a boron neutron capture agent comprising at least nine $^{10}B$ atoms per molecule of the agent in an amount effective to associate the boron neutron capture agent with the tumor cells, and then irradiating the tumor cells with fast neutrons.

Suitable boron neutron capture agents useful in the practice of the invention include multiple $^{10}B$-atom containing compounds that specifically bind to the target cells, or are capable of being specifically targeted to the target cells using targeting vehicles well known to those skilled in the art. For example, the boron neutron capture agents may be based on polyhedral borane anion derivatives, such as closo-$B_{12}H_{12}^{2-}$ (Pitochelli, A. et al., *J. Am. Chem. Soc.* 82: 3228 wherein $M^+$ is an alkali metal cation or tetra alkyl ammonium, as defined above, $R_1$ and $R_2$ are independently selected from hydrogen, groups suitable for linking to a ligand, targeting moieties and other functional groups for conveying desirable properties to the compounds, m is and et seq. (1960); Miller, H., *J. Am. Chem. Soc.* 85: 3885et seq. (1963)), or closo-$B_{10}H_{10}^{2-}$ (Hawthorne, M. F. et al., *J. Am. Chem. Soc.* 81: 5519 et seq. (1959); Lipscomb, A., *J. Am. Chem. Soc.* 81: 5833 et seq. (1959)). A representative, presently particularly preferred compound of this class includes BSH ($B_{12}H_{12}SH^{2-}$; Knoth, W., *J. Am. Chem. Soc.*

86: 3973 et seq. (1964); Tolpin, E. et al., *Inorg. Chem.* 17: 2867 (1978)) that contains a thiol function to permit covalent disulfide bonds with thiol groups presented by serum and tumor proteins.

Alternatively, the boron neutron capture agents of the invention may comprise two polyhedral borane anion cages linked together to form a linked cage structure comprising, for example 20 boron atoms (hereinafter referred to as "B20 compounds"; see M. F. Hawthorne, *Angewandte Chemie, International Edition in English,* 32: 950–984 (1993)). $B_{20}$ compounds of the invention include compounds of the formula $M_nB_{20}H_{17}L$, wherein M is a cation, e.g., an alkali metal or tetra alkyl ammonium cation, n is an integer from 1 to 4, and L is a two electron donor. Preferably, M is Na, K, Cs or Rb, and alkyl includes methyl, ethyl and other alkyls which do not render the resulting salt insoluble. L is a two electron donor, preferably selected from the group consisting of —$NHR_1R_2$ wherein $R_1$ and $R_2$ are the same or different and are selected from the group consisting of hydrogen, benzyl, alkyl and diamine (e.g., ethylene diamine); and —$SR_1R_2$ wherein $R_1$ is selected from the group consisting of hydrogen, benzyl, alkyl and diamine, and $R_2$ is selected from the group consisting of hydrogen, alkyl, —XCN, —XCO, —XNCO, —$XCO_2OH$, —$XCO_2OR$, —$XNHCONHR_1$, —XCOOH, and —$XCONHR_1$, where X is alkyl or arylakyl having from 1 to 20 carbon atoms, and $R_1$ is as defined above. Preferably, L is selected from the group consisting of —$NH_3$, —$NH_2$—$CH_2$—Ph, —$NH_2CH_2CH_2NH_2$ and —$NH_2(CH_2)7CH_3$. Most preferably, L is —$NH_3$.

The boron neutron capture agents may also be based on polyhedral carboranes such as compounds of the formulas closo-$C_2B_{n-2}H_n$ (Dunks, G. et at., *Accts. Chem. Res.* 6: 124 et seq. (1973); Grafstein, J., *Inorg. Chem.* 2: 1128 et seq. (1963)), or closo-$CB_{n-1}H_n$(Knoth, W., *J. Am. Chem. Soc.* 89: 1274 et seq. (1967); Morris, J. et al., *Proceedings of the Fourth International Symposium on Neutron Capture Therapy of Cancer in Progress in Neutron Capture Therapy of Cancer,* Ed. B. Allen et al., Plenum Press, New York, pp. 215 et seq. (1992)), as well as their corresponding nido-derivatives, e.g., compounds of the formula nido-$C_2B_{n-3}H_n$. The o-closo-$C_2B_{10}H_{12}$ carboranes are generally represented by the structure:

including derivatives thereof, while the corresponding anionic o-nido-$C_2B_9H_{12}$ carboranes and their derivatives may be represented as:

where $M^\oplus$ represents a cation, such as an alkali metal cation or tetra alkyl ammonium cation.

More preferably, the boron neutron capture agents of the invention may comprise a plurality of carborane cage structures, such as oligomeric peptides constructed from boron-rich α-amino acids using Merrifield solid phase synthesis methods as disclosed in Varadarajan, M. et al., *Bioconj. Chem.* 2: 242 (1991) and Paxton, R. etal., *Bioconj. Chem.* 3: 243 (1992), the disclosures of which are incorporated herein by reference. Even more preferably, the boron containing agents of the invention may comprise carborane-derived oligophosphates, such as those described in Kane, R. et al., "Automated Syntheses of Carborane-Derived Homogeneous Oligophosphates: Reagents for Use in the Immunoprotein-Mediated Boron Neutron Capture Therapy of Cancer," *J. Am. Chem. Soc.* 115(19): 8853–8854 (1993); Kane, R. et al., "Solution-Phase Synthesis of Boron-Rich Phosphates," *J. Org. Chem.* 58(12): 3227–3228 (1993); and R. Kane et at., "Novel Carboranyl Diols and Their Derived Phosphate Esters," *Advances in Neutron Capture Therapy,* A. H. Soloway et al., Eds., Plenum Press, New York (1993), the disclosures of which are incorporated herein by this reference. Representative compounds of this class include compounds of the formula:

wherein $M^+$ is an alkali metal cation or tetra alkyl ammonium, as defined above, $R_1$ and $R_2$ are independently selected from hydrogen, groups suitable for linking to a ligand, targeting moieties and other functional groups for conveying desirable properties to the compounds, m is an integer from 1 to 10 and n is an integer from 2 to 150, preferably from 20 to 100. As used above, the group is intended to represent a carboranyl cage structure.

The isotopic content of the boron employed in the agents of the present invention can range from the natural abundance of approximately 19.78% $^{10}B$ up to an enriched population of 95% or more of $^{10}B$. Preferably, the isotopic content of the boron employed in the agents of the present invention is at least 75% $^{10}B$, and more preferably at least 85% $^{10}B$, and most preferably at least 95% $^{10}B$.

The boron neutron capture agents of the present invention can be administered either as free agents or in connection with other delivery vehicles, such as unilamellar or multilamellar vesicles, including liposomes. The preparation and use of vesicles in drug delivery applications are well known and documented in the art. See, e.g., Shelly, K. et al., *PNAS* 89: 9039 et seq. (1992), the disclosure of which is incorporated herein by this reference. In one embodiment of the invention, liposome encapsulated tumor treating agents of the invention may include a unilamellar or multilamellar liposome where the liposome comprises at least one encapsulating bilayer and an internal space defined by the encapsulating bilayer. A boron containing agent of the invention may then be encapsulated within the internal space or between the layers of the liposome. A wide variety of lipid particles may form delivery vesicles which are useful in this aspect of the invention. For example, phospholipid lipid vesicles such as those disclosed in EP patent application EP 0272091, the disclosure of which is incorporated herein by this reference, may be employed with the boron containing agents of the present invention. These phospholipid vesicles are composed of a single encapsulating phospholipid membrane associated with an amphiphile-associated substrate. Liposomes of this type may be prepared by methods conventional in the art. For example, a hydrated phospholipid suspension, when agitated, forms multilamellar vesicles, with water separating many bilayers having diameters of 1–10 μm. Application of a shearing or homogenizing force such as sonication to a multilamellar suspension produces small unilamellar vesicles of a size that may range from about 30 to about 250 nm, and more preferably from about 50 to about 100 nm in average diameter. This range is considered to be preferable to obtain optimal circulation time in vivo and target cell specificity. As used herein, "unilamellar" is generally meant to include from one to three, and preferably one, bilayer. The average diameter of the liposome encapsulated borane containing agents of the invention is dependent on many factors, including the sonication time of the phospholipid suspension, the composition of lipid materials employed, the methods by which the liposome is prepared and other relevant factors. Liposomes comprising boron containing agents of the invention embedded in the bilayer of the liposomes can be obtained by the methods disclosed in M. F. Hawthorne, *Angewandte Chemie, International Edition in English*, 32: 950–984 (1993). For example, a dried film may be prepared by dissolving a lipophilic boron containing agent of the invention and a cholesterol:phospholipid mixture in chloroform, and then removing the solvent in vacuo. The resulting dry film is then homogenized by sonication, and the resulting vesicles are separated from free boron containing agent, such as by eluting through a column of Sephadex G-25 (medium) with isotonic phosphate-buffered saline or lactose. The amount of boron embedded in the liposome bilayer is dependent on the amount of boron containing agent added to the original mixture, and can be controlled as desired.

The boron neutron capture agents of the invention may be employed in vitro or in vivo for killing of target cells, e.g., tumor cells. For the boron neutron capture killing of target cells in vitro, the cells are contacted with at least one boron containing agent of the invention, and then the cells are subjected to neutron bombardment from a source that emits fast neutrons. As used herein, the term "fast neutrons" is intended to include neutrons having energies greater than about 50 KeV, more preferably greater than about 100 KeV, and most preferably greater than about 1 MeV. In a representative embodiment, a filtered neutron beam is provided which has a neutron flux greater than $10^{10}$ and preferably greater than about $10^{11}$ n/cm$^2$sec at the treatment site, a neutron energy distribution in which less than about 15% and preferably less than about 5% of the neutrons have energies below 50 KeV. The sample to be treated is positioned so that the target cells are in the path of the beam and are treated for an appropriate length of time. To provide a suitable beam of neutrons, a radiation beam, with neutrons having a wide energy distribution, may be filtered through a filter system that reduces the number of thermal or epithermal neutrons, if desired. Upon contact with tissue, a component of the fast neutron beam diminishes to epithermal, and ultimately to thermal energy levels enabling capture by $^{10}$B.

For in vivo applications, compositions of boron neutron capture agents of the invention generally comprise an amount of a boron effective, when administered to a human or other non-human animal subject together with a pharmaceutically acceptable carrier, to localize a sufficient amount of boron at target tissue sites to enable subsequent neutron irradiation, boron neutron capture and target cell killing. Any pharmaceutically acceptable carder may be generally used for this purpose, provided that the carrier does not significantly interfere with the stability or bioavailability of the boron containing agents of the invention. The human or other non-human animal subject may then be irradiated with fast neutrons, as described above.

The boron neutron capture agents can be administered in any effective pharmaceutically acceptable form to warm blooded animals, including human and other animal subjects, e.g., in topical, lavage, oral, suppository, parenteral, or infusable dosage forms, as a topical, buccal, or nasal spray or in any other manner effective to deliver the boron containing agents to a site of target cells. The route of administration will preferably be designed to optimize delivery and localization of the agents to the target cells.

For topical applications, the pharmaceutically acceptable carder may take the form of liquids, creams, lotions, or gels, and may additionally comprise organic solvents, emulsifiers, gelling agents, moisturizers, stabilizers, surfactants, wetting agents, preservatives, time release agents, and minor amounts of humectants, sequestering agents, dyes, perfumes, and other components commonly employed in pharmaceutical compositions for topical administration.

Compositions designed for injection may comprise pharmaceutically acceptable sterile aqueous or nonaqueous solutions, suspensions or emulsions. Examples of suitable nonaqueous carders, diluents, solvents, or vehicles include propylene glycol, polyethylene glycol, vegetable oils, such as olive oil, and injectable organic esters such as ethyl oleate. Such compositions may also comprise adjuvants such as preserving, wetting, emulsifying, and dispensing agents. They may be sterilized, for example, by filtration through a bacteria-retaining filter, or by incorporating sterilizing agents into the compositions. They can also be manufactured in the form of sterile solid compositions which can be dissolved or suspended in sterile water, saline, or other injectable medium prior to administration.

Solid dosage forms for oral or topical administration include capsules, tablets, pills, suppositories, powders, and granules. In solid dosage forms, the compositions may be admixed with at least one inert diluent such as sucrose, lactose, or starch, and may additionally comprise lubricating agents, buffering agents, enteric coatings, and other components well known to those skilled in the art.

Actual dosage levels of boron neutron capture agents in the compositions of the invention may be varied so as to obtain amounts of the boron containing agent at the site of target cells, especially tumor cells, effective to obtain the desired therapeutic, prophylactic or diagnostic response. Accordingly, the selected dosage level will depend on the nature and site of the target cells, the desired quantity of boron required at the target cells for effective neutron capture or imaging purposes, the nature and boron content of the boron containing agent employed, the route of administration, and other factors. Generally, a sufficient amount of the boron containing agent is employed to attain a boron content of at least about 1 μg/g of target cell tissue, more preferably at least about 10 μg/g of target cell tissue, and most preferably at least about 20 μg/g of target cell tissue.

There are several potential advantages to the fast neutron augmentation approach: (a) it builds on a set of well-established, hospital-based, fast neutron radiotherapy facilities that are located in major metropolitan areas and are experienced in conducting clinical trials; (b)with fast neutron beams it is possible to treat many more tumor systems than the relatively superficial tumors to which low energy reactor beams are restricted; (c)since BNCT is used in the practice of the invention as a "concomitant boost" for the fast neutron beam, the enhanced tumor cell killing can be treated statistically and it may not be necessary to "tag" almost every tumor cell with $^{10}B$ (which is an overwhelming problem in conventional BNCT); and (d)normal tissue tolerance doses have already been well established for fast neutron radiotherapy which provides a means of estimating the safe dose range for clinical trials.

The foregoing may be better understood in connection with the following representative examples, which are presented for purposes of illustration and not by way of limitation.

EXAMPLES

Example 1

In Vitro Tests

V-79 cells (P. Wootton al., *Progress in Neutron Capture Therapy for Cancer*, B. J. Allen et al., Eds., Plenum Press, New York 1992, pp. 195–198) were divided into separate cultures and were cultured in normal media, normal media plus 1mmol boric acid or normal media plus 1 mmol $Na_2B_{12}H_{11}SH$ (BSH) for 24 hours prior to irradiation. Neutrons with a mean energy of 24 MeV were generated through a 50 MeV proton on beryllium reaction in a hospital-based Scanditronix cyclotron. A 20 ×20 collimated field size results in favorable conditions for BNCT enhancement for this system (see G. E. Laramore et al., "Boron Neitron Capture Therapy: A Mechanism For Achieving a Concomitant Tumor Boost in Fast Neutron Radiotherapy," *Int. J. Radiat. Oncol. Biol. Phys.*, 1994). Replicate samples for each of the normal media, normal media plus boric acid and normal media plus BSH cultures were subjected to total irradiation doses of 0 (sham irradiation), 2.5, 5, 10 or 15 Gy. Following irradiation, the cells of each sample were trypsinized, counted and plated at 3 different concentrations. The plating efficiencies for the normal, BSH and boric acid were relatively equal, varying between 50% and 60% on the sham-irradiated controls. The higher irradiation doses, 10 and 15 Gy exhibited higher than expected cell survival resulting in confluent cultures rather than countable colonies.

The survival of cells for each of the media after an irradiation dose of 5 Gy is shown in the following Table 1:

TABLE 1

In Vitro Irradiation
V-79 Cell Culture
Radiation Dose = 5 Gy

| Media | No. Cells Plated | | | No. Colonies | | | Mean |
|---|---|---|---|---|---|---|---|
| | Plate 1 | Plate 2 | Plate 3 | Plate 1 | Plate 2 | Plate 3 | Survival %[1] |
| Normal Media | 300 | 580 | 600 | 6 | 18 | 8 | 4.3 |
| Media + 1 mM Boric Acid | 2000 | 3000 | 4000 | 37 | 37 | 30 | 2.3 |
| Media + 1 mM BSH | 2000 | 3000 | 4000 | 5 | 13 | 18 | 0.8 |

Note: Plating efficiency controls were similar for all groups at 50%.

Figure 1:
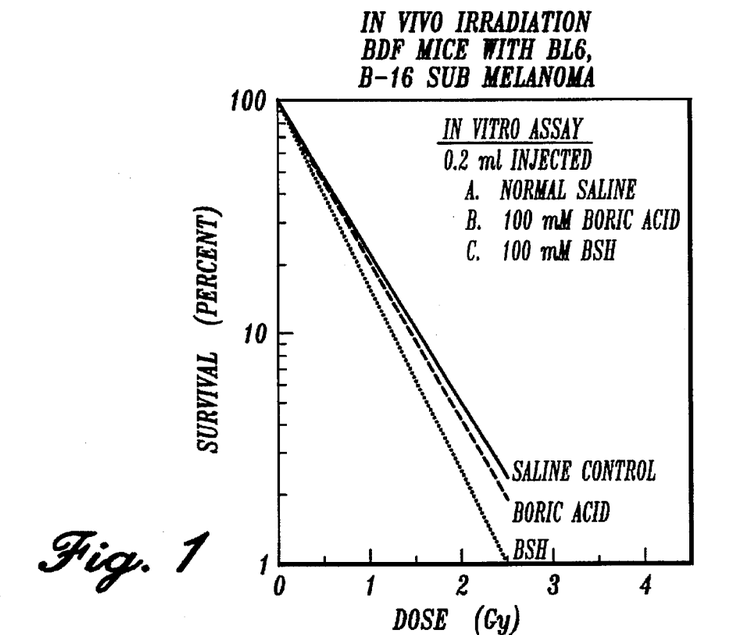
FIG. 1 is a graphical representation of the percentage survival of V79 cells when subjected to fast neutron bombardment in vitro at 5 Gy in the presence of normal medium, normal medium plus 1.0 mM boric acid, or normal medium plus 1.0 mM BSH, as described in Example 1.

[1] $\text{Survival \%} = \frac{\text{No. Colonies Counted}}{\text{No. Cells Plated}} \times \frac{1}{\text{Plating Efficiency}} \times 100$ A plot of the 5 Gy sample irradiated specimens is shown in FIG. 1. From the foregoing, it can be seen that BSH exhibited significantly enhanced cell killing over the boric acid treated sample and over the control.

Example 2

In Vivo Tests

Mice of the BDF strain were implanted with BL-6, B-16 tumor cells (C. A. Elstad et al., "In vivo and in vitro Uptake of Boronated Compounds by B 16-BL6 Murine Melanoma," *Advances in Neutron Capture Therapy* (A. H. Soloway et at., Eds.), Plenum Press, New York, N.Y. pp. 619–622 (1993)) in the right dorsal hip region, and were injected with 0.2 ml of either saline, 100 mmol solution of boric acid or 100 mmol solution of BSH. The mice were lightly anesthetized with isoflurane and then housed in a plexiglass grid and were irradiated one hour after injection to doses of 0 (sham-irradiated), 2.5 and 10 Gy, as described in Example 1. The mice were later sacrificed by halothane anesthesia and cervical dislocation, and the tumors were excised, minced, digested with collagenase, the cell density was counted and then samples were plated at 3 separate dilutions. Resulting colonies were counted 10–12 days later.

The survival of cells at the 2.5 Gy irradiation dose level is shown in the following Table 2:

TABLE 2

In Vivo Experiment
B-16 Cells Sub Q in CBA Mice
In Vitro Assay Postirradiation

| Injected drug Mouse group | Plating Efficiency | No. Cells Plated | | | No. Colonies Counted | | | Mean Survival %[1] |
|---|---|---|---|---|---|---|---|---|
| | | Plate 1 | Plate 2 | Plate 3 | Plate 1 | Plate 2 | Plate 3 | |
| Saline | 0.093 | 150 | 300 | 450 | 0 | 2 | 0 | 2.3 |
| 0.2 ml 100 mM Boric Acid | 0.057 | 200 | 300 | 400 | 0 | 1 | 0 | 1.9 |
| 0.2 ml 100 mM Boric Acid | 0.080 | 200 | 300 | 400 | 0 | 0 | 0 | <1.0 |

Figure 2:
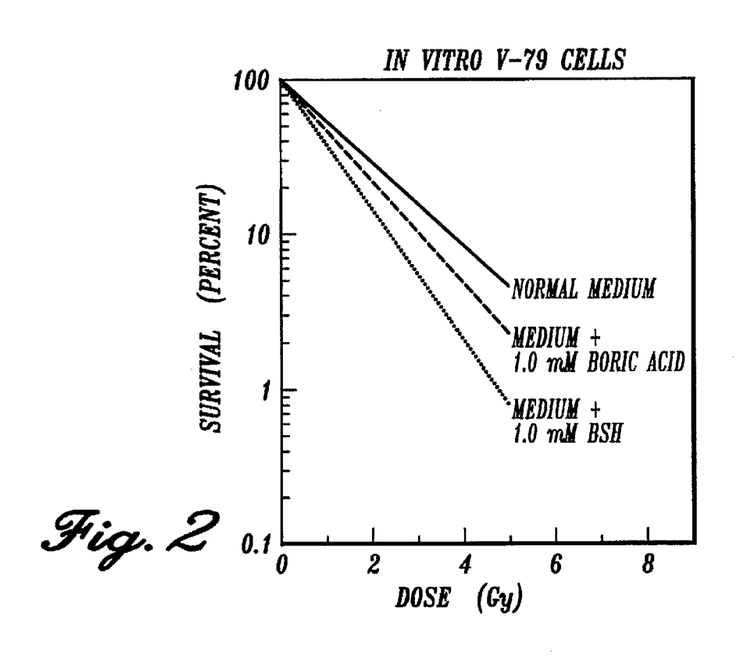
FIG. 2 is a graphical representation of the percentage survival of BL-6, B-16 tumor cells when subjected to fast neutron bombardment in vivo in BDF mice at 2.5 Gy after injection of 0.2 ml of normal saline, 100 mM boric acid, or 100 mM BSH, as described in Example 2.

[1] $\text{Survival \%} = \frac{\text{No. Colonies Counted}}{\text{No. Cells Plated}} \times \frac{1}{\text{Plating Efficiency}} \times 100$ The percentage of cell survival in the three groups at a radiation dose of 2.5 Gy is shown in FIG. 2. From the foregoing, it is concluded that cell killing in the BSH treated group was over twice that of the boric acid treated or control groups.

The use of boron neutron capture agents of the invention in connection with fast neutron therapy overcomes many problems associated with conventional BNCT or fast neutron therapy alone. For example, there are domestic and pragmatic problems with using thermal or epithermal neutrons. These low energy neutrons have poor tissue penetration, making the treatment of deep-seated tumors impractical. Most of the work with BNCT has utilized a nuclear reactor as the source of thermal neutrons. Reactor-based treatments are limited by their cost, concerns over the reactor safety and long term potential environmental consequences, the distance of the treatment reactor from a medical facility, and the political uncertainty of their future. These limitations of traditional BNCT are overcome in the practice of the invention by using boron neutron capture in conjunction with fast neutron radiotherapy. The apparent disadvantage inherent combining BNCT with fast neutron therapy, i.e., that the probability of boron neutron capture events is much less for fast neutrons than for traditional reactor-based treatment, is overcome by the use of the boron neutron capture agents of the present invention. Apart from resonance effects, the probability of BNCT events is inversely related to the square root of the energy of the neutron beam (S. DeBenedetti, in *Nuclear Interactions*, John Wiley & Sons, New York, N.Y., pp. 338–344 (1964)). Fast neutrons have energies $10^7$-fold greater than those of thermal neutrons generated in a nuclear reactor. To use BNCT as a mechanism of enhancing fast neutron radiation, a sufficient percentage of fast neutrons must be degraded to thermal energies at tumor depth to permit sufficient BNCT events to enhance the efficacy of fast neutron radiation (G. E. Laramore, *Int. J. Radial. Oncol. Biol. Phys.*, (1994), supra). This enhancement is dependent on the concentration of $^{10}$B within tumors, which is achieved at high levels with the boron neutron capture agents disclosed herein.

The advantages of using BNCT to enhance fast neutron radiation are numerous. Using BNCT as a selective tumor boost during fast neutron radiation mitigates the need for every tumor cell to be labeled with $^{10}$B in order to achieve "tumor cure." Furthermore, treatments are given with hospital-based cyclotrons, alleviating the safety and environmental concerns of reactor-based treatment facilities. Fast neutron therapy is performed with isocentric treatments and irregularly shaped, customized fields. The high energy neutrons used in fast neutron radiation provide depth-dose distributions similar to modern day linear accelerators, and the depth of the thermal neutron beam component can be controlled to some degree through modification of beam generating conditions. These features permit BNCT with fast neutron radiation to treat both superficial and deep-seated tumors, allowing greater clinical applicability than that possible with traditional BNCT.

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. A method of killing target cells comprising irradiating the cells with a neutron beam from a source that emits neutrons having an energy distribution in which less than about 15% of the neutrons have energies below 100 KeV in the presence of a boron neutron capture agent comprising at least nine boron atoms per molecule of the agent.

2. The method of claim 1 wherein the boron neutron capture agent is enriched in $^{10}$B and the target cells are irradiated with fast neutrons in vitro.

3. The method of claim 1 wherein the boron neutron capture agent is enriched in $^{10}$B and the target cells are irradiated with fast neutrons in vivo.

4. The method of claim 1 wherein the target cells are tumor cells.

5. The method of claim 1 wherein the boron neutron capture agent comprises a polyhedral borane derivative or a polyhedral carborane derivative.

6. The method of claim 5 wherein the boron neutron capture agent comprises a polyhedral borane derivative selected from the group consisting of compounds of the formulas (1) closo-$B_nH_n^{2-}$, (2) closo-$B_nH_{n-1}SH^{2-}$, and (3) $M_mB_{20}H_{17}L$, wherein M is an alkali metal or tetra alkyl ammonium cation, m is an integer from 1 to 4, n is and integer from 10 to 12, and L is a two electron donor.

7. The method of claim 6 wherein the polyhedral borane derivative is selected from the group consisting of closo-$B_{12}H_{12}^{2-}$, closo-$B_{10}H_{10}^{2-}$, closo-$B_{12}H_{12}SH^{2-}$, and $Na_4B_{20}H_{17}NH_3$.

8. The method of claim 5 wherein the wherein the boron neutron capture agent comprises a polyhedral carborane compound selected from the group consisting of o-closo- $C_2B_{10}H_{12}$ carboranes, anionic o-nido-$C_2B_9H_{12}^-$ carboranes and derivatives thereof comprising a plurality of carborane cage structures.

9. The method of claim 8 wherein the boron neutron capture agent comprises a plurality of carborane cage structures linked together as oligomeric peptides.

10. The method of claim 8 wherein the boron neutron capture agent comprises an oligophosphate compound of the formula:

wherein $M^+$ is an alkali metal cation or tetra alkyl ammonium, $R_1$ and $R_2$ are independently selected from hydrogen or a linking group, m is an integer from 1 to 10 and n is an integer from 2 to 150.

11. A method of treating tumor cells in a human or non-human animal comprising administering to the human or non-human animal a boron neutron capture agent comprising at least nine $^{10}B$ atoms per molecule of the agent in an amount effective to associate the boron neutron capture agent with the tumor cells, and then irradiating the tumor cells with a neutron beam from a source that emits neutrons having an energy distribution in which less than about 15% of the neutrons have energies below 100 Kev.

12. The method of claim 11 wherein the boron neutron capture agent comprises a polyhedral borane derivative or a polyhedral carborane derivative.

13. The method of claim 12 wherein the boron neutron capture agent comprises a polyhedral borane derivative selected from the group consisting of compounds of the formulas (1) closo-$B_nH_n^{2-}$, (2) closo-$B_nH_{n-1}SH^{2-}$, and (3) $M_mB_{20}H_{17}L$, wherein M is a cation, e.g., an alkali metal or tetra alkyl ammonium cation, m is an integer from 1 to 4, n is an integer from 10 to 12, and L is a two electron donor.

14. The method of claim 13 the polyhedral borane derivative is selected from the group consisting of closo-$B_{12}H_{12}^{2-}$, closo-$B_{10}H_{10}^{2-}$, closo-$B_{12}H_{12}SH^{2-}$, and $Na_4B_{20}H_{17}NH_3$.

15. The method of claim 12 wherein the wherein the boron neutron capture agent comprises a polyhedral carborane compound selected from the group consisting of o-closo-$C_2B_{10}H_{12}$ carboranes, anionic o-nido-$C_2B_9H_{12}$ carboranes and derivatives thereof comprising a plurality of carborane cage structures.

16. The method of claim 15 wherein the boron neutron capture agent comprises a plurality of carborane cage structures linked together as oligomeric peptides.

17. The method of claim 15 wherein the boron neutron capture agent comprises an oligophosphate compound of the formula:

wherein $M^+$ is an alkali metal cation or tetra alkyl ammonium, $R_1$ and $R_2$ are independently selected from hydrogen or a linking group, m is an integer from 1 to 10 and n is an integer from 2 to 150.

18. The method of claim 11 wherein the boron neutron capture agent is administered to the human or non-human animal in a unilamellar or multilamellar vesicle.

19. The method of claim 18 wherein the unilamellar or multilamellar vesicle comprises at least one encapsulating bilayer that defines an internal space, and the boron neutron capture agent is encapsulated in the internal space.

20. The method of claim 18 wherein the unilamellar or multilamellar vesicle comprises at least one encapsulating bilayer, and the boron neutron capture agent is encapsulated between the layers of the vesicle.

21. The method of claim 18 wherein the unilamellar or multilamellar vesicle comprises at least one encapsulating bilayer, and a lipophilic boron species is dissolved in the bilayer.

* * * * *

UNITED STATES PATENT AND TRADEMARK OFFICE
CERTIFICATE OF CORRECTION

PATENT NO. : 5,630,786      Page 1 of 6
DATED : May 20, 1997
INVENTOR(S) : B.R. Griffin et al.

It is certified that error appears in the above-indentified patent and that said Letters Patent is hereby corrected as shown below:

| <u>COLUMN</u> | <u>LINE</u> | |
|---|---|---|
| TITLE PAGE: | | |
| Item [56] Pg. 2, col. 2 | Refs. Cited (Item 30) | After "Boranes" insert --.-- |
| [56] Pg. 2, col. 2 | Refs. Cited (Item 35) (9th Ref.) | ""1-$B_9H_9$CH-and $B_{11}H_{11}$CH-,"" should read --"1-$B_9H_9$CH⁻ and $B_{11}H_{11}$CH⁻,"-- |
| [56] Pg. 2, col. 2 | Refs. Cited (Item 38) | After "Evaluation" delete "." and insert --,-- |
| [56] Pg. 2, col. 2 | Refs. Cited (Item 39) | "Carborane-D-erived" should read --Carborane-Derived-- |
| [56] Pg. 2, col. 2 | Refs. Cited (Item 39) | "Immuno-protein-Mediated" should read --Immunoprotein-Mediated-- |
| 14 | 40 | After "KeV" insert --,-- |
| 14 | 59-60 | "n is and integer" should read --n is an integer-- |
| 14 | 65 | Delete "wherein the" (second occurrence). |

UNITED STATES PATENT AND TRADEMARK OFFICE
CERTIFICATE OF CORRECTION

PATENT NO. : 5,630,786  
DATED : May 20, 1997  
INVENTOR(S) : B.R. Griffin et al.

Page 2 of 6

It is certified that error appears in the above-indentified patent and that said Letters Patent is hereby corrected as shown below:

| COLUMN | LINE | |
|---|---|---|
| 15/16 | 12-20 | Formula in Claim 10 should read: |

--

; or

--

| | | |
|---|---|---|
| 15 | 49 | "Kev." should read --KeV.-- |
| 15 | 60 | After "Claim 13" insert --wherein-- |
| 15 | 64 | Delete "wherein the" (second occurrence) |

UNITED STATES PATENT AND TRADEMARK OFFICE
CERTIFICATE OF CORRECTION

PATENT NO.   :   5,630,786
DATED        :   May 20, 1997
INVENTOR(S)  :   B.R. Griffin et al.

It is certified that error appears in the above-indentified patent and that said Letters Patent is hereby corrected as shown below:

| COLUMN | LINE | |
|---|---|---|
| 15/16 | 30-38 | Formula in Claim 17 should read: |

--

; or

--

| | | |
|---|---|---|
| 1 | 21 | "borons" should read --boron's-- |
| 2 | 60 | "P.A. Zahl et at.," should read --P.A. Zahl et al.,-- |
| 2 | 66 | "carded" should read --carried-- |
| 3 | 2-3 | "L.E. Farr et at.," should read --L.E. Farr et al.,-- |
| 3 | 3 | "inthe" should read --in the-- |
| 3 | 31 | "Tumors. II.,"" should read --Tumors. I.,"-- |

UNITED STATES PATENT AND TRADEMARK OFFICE
CERTIFICATE OF CORRECTION

PATENT NO. : 5,630,786
DATED : May 20, 1997
INVENTOR(S) : B.R. Griffin et al.

It is certified that error appears in the above-indentified patent and that said Letters Patent is hereby corrected as shown below:

| COLUMN | LINE | |
|---|---|---|
| 3 | 46 | "carder" should read --carrier-- |
| 4 | 4 | "(P.H. Gutin et at.," should read --(P.H. Gutin et al.,-- |
| 4 | 7-8 | "*Radiosensitivies*" should read --*Radiosensitivities*-- |
| 4 | 14-15 | "(T.W. Griffin et at.," should read --(T.W. Griffin et al.,-- |
| 4 | 46 | "Trial,"in" should read --Trial," *Am.*-- |
| 4 | 54 | "supra))." should read --supra).-- |
| 5 | 67 | "m is and" should read --m is an-- |
| 6 | 62 | "85:3885et seq." should read --85:3885 et seq.-- |
| 7 | 8 | ""B20" should read --"$B_{20}$-- |
| 7 | 29 | "-$NH_2(CH_2)7CH_3$." should read --$NH_2(CH_2)_7CH_3$.-- |
| 7 | 33 | "(Dunks, G. et at.," should read --(Dunks, G. et al.,-- |
| 7 | 48 | "closo-$CB_{n-1}H_n$(Knoth," should read --closo-$CB_{n-1}H_n$- (Knoth,-- |
| 7 | 54 | "nido-$C_2B_{n-3}H_n$." should read --nido-$C_2B_{n-3}H_n$-.-- |

UNITED STATES PATENT AND TRADEMARK OFFICE
CERTIFICATE OF CORRECTION

PATENT NO. :     5,630,786
DATED     :     May 20, 1997
INVENTOR(S) :     B.R. Griffin et al.

It is certified that error appears in the above-indentified patent and that said Letters Patent is hereby corrected as shown below:

| COLUMN | LINE | |
|---|---|---|
| 8 | 15 | "Paxton, R. etal.," should read --Paxton, R. et al.,-- |
| 8 | 27 | "R. Kane et at.," should read --R. Kane et al.,-- |
| 10 | 20 | "carder" should read --carrier-- |
| 10 | 36 | "carder" should read --carrier-- |
| 10 | 46 | "carders," should read --carriers,-- |
| 11 | 47 | "trials," should read --trials.-- |
| 11 | 57 | Before "al.," insert --et-- |
| 12 | 1 | "Neitron" should read --Neutron-- |
| 12 | 51 | "B 16-BL6" should read --B16-BL6-- |
| 12 | 52 | "(A.H. Soloway et at.," should read --(A.H. Soloway et al.,-- |

UNITED STATES PATENT AND TRADEMARK OFFICE
CERTIFICATE OF CORRECTION

PATENT NO. : 5,630,786
DATED : May 20, 1997
INVENTOR(S) : B.R. Griffin et al.

It is certified that error appears in the above-identified patent and that said Letters Patent is hereby corrected as shown below:

13   57   "*Radial.*" should read --*Radiat.*--

Signed and Sealed this

Fourteenth Day of April, 1998

Attest:

BRUCE LEHMAN

*Attesting Officer*   *Commissioner of Patents and Trademarks*